US011819555B2

(12) United States Patent
O'Heeron

(10) Patent No.: US 11,819,555 B2
(45) Date of Patent: Nov. 21, 2023

(54) GENE THERAPY FOR THE REGENERATION OF CHONDROCYTES OR CARTILAGE TYPE CELLS

(71) Applicant: Figene, LLC, Houston, TX (US)

(72) Inventor: Pete O'Heeron, Houston, TX (US)

(73) Assignee: Figene, LLC, Houston, TX (US)

( * ) Notice: Subject to any disclaimer, the term of this patent is extended or adjusted under 35 U.S.C. 154(b) by 0 days.

(21) Appl. No.: 14/917,560

(22) PCT Filed: Sep. 9, 2014

(86) PCT No.: PCT/US2014/054804
§ 371 (c)(1),
(2) Date: Mar. 8, 2016

(87) PCT Pub. No.: WO2015/035395
PCT Pub. Date: Mar. 12, 2015

(65) Prior Publication Data
US 2016/0220699 A1  Aug. 4, 2016

Related U.S. Application Data

(60) Provisional application No. 61/875,509, filed on Sep. 9, 2013.

(51) Int. Cl.
*A61K 48/00* (2006.01)
*C12N 5/10* (2006.01)
*C12N 15/85* (2006.01)

(52) U.S. Cl.
CPC ...... *A61K 48/0058* (2013.01); *A61K 48/0075* (2013.01); *C12N 5/10* (2013.01); *C12N 15/85* (2013.01); *C12N 2800/107* (2013.01)

(58) Field of Classification Search
CPC . A61K 48/00; A61K 48/0058; A61K 48/0075
See application file for complete search history.

(56) References Cited

U.S. PATENT DOCUMENTS

| | | | |
|---|---|---|---|
| 6,197,586 B1 | 3/2001 | Bhatnagar et al. | |
| 6,413,511 B1 | 7/2002 | Glorioso et al. | |
| 6,537,540 B1 | 3/2003 | Burstein et al. | |
| 6,737,413 B2 * | 5/2004 | Koopman | C07K 14/4705 424/93.2 |
| 7,282,200 B2 * | 10/2007 | Song | A61K 35/32 424/93.1 |
| 7,482,114 B2 * | 1/2009 | Luyten | A61K 49/0004 435/4 |
| 7,846,428 B2 | 12/2010 | Fisher | |
| 2004/0191900 A1 | 9/2004 | Mizuno et al. | 435/366 |
| 2007/0184033 A1 | 8/2007 | Sevrain et al. | 424/93.7 |
| 2008/0187576 A1 | 8/2008 | Ghivizzani et al. | |
| 2008/0226611 A1 | 9/2008 | Noh et al. | |
| 2009/0068270 A1 | 3/2009 | Attawia et al. | 424/484 |
| 2009/0202653 A1 | 8/2009 | Erwin et al. | |
| 2011/0038924 A1 | 2/2011 | Goomer | |
| 2012/0045419 A1 | 2/2012 | Erwin et al. | |
| 2013/0090290 A1 * | 4/2013 | Qin | C07K 14/51 514/8.8 |
| 2014/0286912 A1 | 9/2014 | Ionescu Silverman et al. | |
| 2014/0287501 A1 | 9/2014 | Kukekov et al. | |
| 2020/0093961 A1 | 3/2020 | Gazit et al. | |

FOREIGN PATENT DOCUMENTS

| | | | | |
|---|---|---|---|---|
| EP | 2034010 A1 | 3/2009 | | |
| JP | H10-509873 A | 9/1998 | | |
| JP | 2002185016 A | 6/2002 | | |
| JP | 2002542801 A | 12/2002 | | |
| JP | 2003/125787 A | 5/2003 | | |
| JP | 2010528222 A | 8/2010 | | |
| WO | 96/17057 A1 | 6/1996 | | |
| WO | 00/66177 | 11/2000 | | |
| WO | 01-013960 A1 | 3/2001 | | |
| WO | WO 2001/13960 | * 3/2001 | ............. A61K 48/00 | |
| WO | 2009046464 A1 | 4/2009 | | |
| WO | 2010/088775 A1 | 8/2010 | | |

(Continued)

OTHER PUBLICATIONS

Pan et al., Sox9, a Key Transcription Factor of Bone Morphogenetic Protein-2-Induced Chondrogenesis, is Activated Through BMP Pathway and a CCAAT Box in the Proximal Promoter. J. Cell. Physiol. 217: 228-241, 2008. (Year: 2008).*
Ikeda et al., The Combination of SOX5, SOX6, and SOX9 (the SOX Trio) Provides Signals Sufficient for Induction of Permanent Cartilage. ARTHRITIS & RHEUMATISM. vol. 50, No. 11, Nov. 2004, pp. 3561-3573. (Year: 2004).*
Clonetech Lab. Inc. Product Sheet, Adeno-X Expression System, pShuttle Vector Information, 2000, pp. 1-2 (Year: 2000).*
Shao et al., Generation of iPS cells using defined factors linked via the self cleaving 2A sequences in a single open reading frame. Cell Res. Mar. 2009 ; 19(3): 296. (Year: 2009).*
Wu et al., Proteolysis Involving Matrix Metalloproteinase 13 (Collagenase-3) Is Required for Chondrocyte Differentiation That Is Associated with Matrix Mineralization. Journal of Bone and Mineral Research. 2002, 17:639-651 (Year: 2002).*

(Continued)

*Primary Examiner* — Arthur S Leonard
(74) *Attorney, Agent, or Firm* — Norton Rose Fulbright US LLP

(57) ABSTRACT

Embodiments of the invention concern the regeneration of chondrocytes and cartilage-type cells. In certain embodiments, one or more genes are employed for the regeneration of chondrocytes and cartilage-type cells. In particular embodiments, one or more gene therapy regimens are employed for the regeneration of chondrocytes and cartilage-type cells. In particular aspects, embodiments concern cartilage repair, such as articular cartilage repair. More particularly, embodiments for the disclosure concern using gene therapy for the attraction, generation and/or regeneration of chondrocytes or other cartilage-type cells and/or the generation and/or repair of cartilage tissue. In specific embodiments of the disclosure, gene therapy is provided that is capable of attracting and/or generating desired cells in vivo.

10 Claims, No Drawings

(56) References Cited

FOREIGN PATENT DOCUMENTS

| WO | 2013/070880 A1 | 5/2013 |
|---|---|---|
| WO | 2014/026012 A2 | 2/2014 |
| WO | 2014/204806 A2 | 12/2014 |
| WO | 2015/035395 A1 | 3/2015 |

OTHER PUBLICATIONS

Szymczak Al, Workman CJ, Wang Y, et al. Correction of multi-gene deficiency in vivo using a single 'self-cleaving' 2A peptide-based retroviral vector. Nat Biotechnol 2004;22:589-594. (Year: 2004).*

Sloten, Audekercke, and van der Perre, "Biomechanica voor tissue engineering: kwantificeren van de mechanische belasting in de knie in Vitro en in Vivo" Katholieke Universiteit Leuven, 2000. (Partial English translation included).

Steinert et al., "Concepts in gene therapy for cartilage repair", Injury, Int. J. Care Injured (2008) 3951, S97-S113.

Tsuchiya et al., "Chonodrogenesis enhanced by overexpression of sox 9 gene in mouse bone marrow-derived mesenchymal stem cells", Biochemical and Biophysical Research Communications, 301 (2003) 338-343.

Shi et al., "Growth Factor Transgenes Interactively Regulate Articular Chondrocytes", J. Cellular Biochemistry, 114:908-919 (2013).

Kazantseva, MG, et al.; "MMP Expression in Rheumatoid Inflammation: The rs11568818 Polymorphism is Associated with MMP-7 Expression at an Extra-Articular Site"; Genes and Immunity' Jan. 24, 2013; 14, 162-169.

Itoh, Yoshifumi; "Metalloproteinases in Rheumatoid Arthritis: Potential Therapeutic Targets to Improve Current Therapies"; Progress in Molecular Biology and Translational Science, vol. 148,; Chapter 8; 2017.

Burrage, Peter S., et al.; "Matrix Metalloproteinases: Role in Arthritis"; Frontiers in Bioscience; 11, 529-543; Jan. 1, 2006.

Brayda-Bruno et al. "Advances in the diagnosis of degenerated lumbar discs and their possible clinical application." European Spine Journal 23.3 (2014): 315-323 (Year: 2014).

Sakai et al. "Exhaustion of nucleus pulposus progenitor cells with ageing and degeneration of the intervertebral disc." Nature Communications 3.1 (2012): 1-11 (Year: 2012).

Erwin et al., NASS 31st Annual Meeting Proceedings / The Spine Journal 16 (2016) S113-S250, S169, No. 117.

Feng et al., "Hypoxia differentially regulates human nucleus pulposus and annulus fibrosus cell extracellular matrix production in 3D scaffolds", Osteoarthritis and Cartilage 21 (2013) 582-588.

Gruber et al., "Three-dimensional culture of human disc cells within agarose or a collegan sponge: assessment of proteoglycan production", Biomaterials 27 (2006) 371-376.

Hunter et al., "The Notochordal Cell inthe Nucleus Pulposus: A Review in the Context of Tissue Enigneering", Tissue Engineering, vol. 9, No. 4, 2003, pp. 667-677.

Jackson, Alicia R., "Notochordal Nucleus Pulposus Cells: Prospective Strategies for Intervertebral Disc Repair and Regeneration", Current Tissue Engineering, 2015, 4, 77-85.

Pereira et al., "Hydrogels in acellular and cellular strategies for intervertebral disc regeneration", J Tissue Eng Regen Med 2013; 7: 85-98.

Risbud et al., "Notochordal Cells in the Adult Intervertebral Disc: New Perspective on an Old Question", Crit Reve Eukaryot Gene Expr. 2011; 21(1): 29-41.

Tang et al., "A new non-enzymatic method for isolating human intervertebral disc cells preserves the phenotype of nucleus pulposus cells", Cytotechnology (2014) 66:979-986.

Wang et al., "Cell and molecular biology of intervertrbral disc degeneration: current understanding and implications for potential therapeutic stategties", Cell Prolif., 2014, 47, 381-390.

Macrophage Elastase—an overview. ScienceDirect. 2021. [retrieved on Aug. 13, 2021]. Retrieved from <https://www.sciencedirect.com/topics/medicine-and-dentistry/macrophage-elastase>.

Pittayapruek, P., et al. (2016) "Role of matrix metalloproteinases in photoaging and photocarcinogenesis." International journal of molecular sciences, vol. 17, issue 6, 868, pp. 1-20. https://doi.org/10.3390/ijms17060868.

Wang et al., "Enhancing intervertebral disc repair and regeneration through biology: platelet-rich plasma as an alternative strategy," Arthritis Res. Ther., 15(5):220, 2013.

J. Christopher Mizer, et al.; "Exogenous Endothelial Cells as Accelerators of Hematopoietic Reconstitution," Jouranl of Translational Medicine; BioMed Central; 2017.

Satoshi Kubota, et al.; "Role of CCN2/CTGF/Hcs24 in Bone Growth," International Review of Cytology, vol. 257, 2007.

Xiao-ming Meng, et al.; "TGF-β: The Master Regulator of Fibrosis," Nature Reviews | Nephrology, 2016 Macmillian Publishers.

Pradeep Ramalingam, et al; Endothelial mTor Maintains Hematopoiesis During Aging, Rockefeller University Press; J. Exp. Med 2002, vol. 217, No. 6.

Feng et al., "Advances on the phenotype of nucleus pulposus cells in interveterbral disc," J. Southeast University (Med. Sci. Edi.), 34(3):443-44, 2015.

Bi et al., "Sox9 is required for cartilage formation," Nature Genetics, 22(1):85-89, 1999.

Office Communication issued in European Patent Application No. 14841529.2, dated Jun. 23, 2022.

Sekiya et al., "In vitro cartilage formation by human adult stem cells from bone marrow stroma defines the sequence of cellular and molecular events during chondrgenesis," Proceedings of the National Academy of Sciences, 99(7):43974402, 2002.

Chen et al., "Tissue-Engineered Intervertebral Disc and Chondrogenesis Using Human Nucleus Pulposus Regulated through TGF-β1 in Platelet-Rich Plasma," Journal of Cellular Physiology, 209:744-754, 2006.

English Translation of Office Communication issued in Japanese Patent Application No. 2021-165865, dated Nov. 29, 2022.

* cited by examiner

GENE THERAPY FOR THE REGENERATION OF CHONDROCYTES OR CARTILAGE TYPE CELLS

CROSS-REFERENCE TO RELATED APPLICATIONS

This application is a national phase application under 35 U.S.C. § 371 that claims priority to International Application No. PCT/US2014/054804 filed Sep. 9, 2014, which claims priority to U.S. Provisional Patent Application Ser. No. 61/875,509 filed Sep. 9, 2013, all of which are incorporated herein by reference in their entirety.

FIELD OF THE INVENTION

The present invention generally concerns at least the fields of medicine, surgery, anatomy, biology, cell biology, and/or molecular biology.

BACKGROUND OF THE INVENTION

Cartilage Degeneration

Joint and articular cartilage injuries are frequent occurrences; over 6 million people visit hospitals in the U.S. each year for various knee, wrist, and ankle problems. Progressive wear and tear on articular cartilage can lead to a progressive cartilage tissue loss, further exposing the bony ends, leaving them without protection. This finally deteriorates into the most common arthritis—osteoarthritis (or degenerative joint disease).

It has been reported that osteoarthritis affects 33.6% (12.4 million) of adults age 65 and older in the U.S. The American Academy of Orthopaedic Surgeons (AAOS) reports that osteoarthritis is a primary diagnosis accounting for 67% of short-stay and nonfatal hospitalizations in 2004. Considering the increasing population, especially in the elderly with longer life expectancies, occurrences of injuries and osteoarthritis will undoubtedly increase, not only in the U.S., but world-wide.

Three types of cartilage exist in the human body: hyaline cartilage (e.g., within diarthrodial joints), fibrocartilage (e.g., knee meniscus and TMJ disc), and elastic cartilage (e.g., ear). Specifically, articular cartilage covering bone surfaces is a soft and specialized hyaline cartilage that exhibits superior lubrication, wear, and low friction properties; it also reduces stresses in the joint.

Articular cartilage is composed of a small percentage of chondrocytes, but a dense extracellular matrix (ECM) prevents chondrocyte mobility. In addition, articular cartilage lacks vascular, neural, and lymphatic networks, as well as various local progenitor cells. It has also been described as having high levels of protease inhibitors, which may inhibit efficient tissue repair.

For these reasons, currently it is challenging to restore full tissue function in damaged or diseased articular cartilage. Although traditional methods like autografts and allografts have been clinically employed to treat articular cartilage lesions, there still exist many shortcomings associated with these therapies. Autografts, which require the transplantation of a small portion of low-weight-bearing cartilage from the patient into defect sites, have disadvantages such as donor site morbidity and limited cartilage tissue availability. Allografts, cartilage pieces obtained from tissue banks, may potentially induce immune responses.

For patients with severe joint damage and osteoarthritis, total joint replacement surgery is needed. However, many complications such as inflammation, infection, and implant loosening frequently occur after joint replacement and may lead to implant failure, necessitating future revision surgery. In fact, nearly 36,000 revisions for 328,000 hip replacements (11%) and 33,000 revisions for 418,000 knee replacements (8%) were performed in the U.S. in 2003 because of failed hip and knee replacements.

Therefore, it is desirable to develop an efficient and simple method to successfully repair and regenerate articular cartilage tissues. As a rapidly expanding field, tissue engineering may provide alternative solutions for articular cartilage repair and regeneration through developing biomimetic tissue substitutes. Typically, articular cartilage is a tissue that is not naturally regenerated once damaged. Recently, efforts have been made to reconstruct damaged biological tissues by regenerating a portion of the damaged tissues in laboratories. This approach, defined as "tissue engineering" has raised tremendous attention.

Tissue engineering involves the development of biocompatible materials capable of specifically interacting with biological tissues to produce functional tissue equivalents. Tissue engineering has a basic concept of collecting a desired tissue from a patient, isolating cells from the tissue specimen, proliferating cells, and re-introducing those cells back into the body.

In particular cases, genes are utilized as therapeutic compositions for the regeneration of biological tissue. In certain cases, such as the regeneration of cardiac biological tissue, the genes Gata4, Mef2C and Tbx5 have been shown to produce cardiomyocytes in some patients. These genes have been researched to attract fibroblasts and induce their differentiation into cardiomyocytes. However, there is no current scientific evidence to support the use of gene therapy in cartilage regeneration. In fact, the heart and joint environments are completely different. Cardiomyocyte exist in heart tissue, which is vascular and has ready access to nutrient flow and oxygen. Cartilage, on the other hand, is considered avascular, aneural and has much less access to oxygen. For these reasons, the two environments are considerably drastically different and, as such, would require different biological approaches to regenerate the tissue.

The present disclosure provides a solution for a long-felt need in the art of cartilage tissue repair or regeneration.

SUMMARY OF THE INVENTION

Embodiments of the invention concern the regeneration of chondrocytes and cartilage-type cells. In certain embodiments, one or more genes are employed for the regeneration of chondrocytes and cartilage-type cells. In particular embodiments, one or more gene therapy regimens are employed for the regeneration of chondrocytes and cartilage-type cells. In particular aspects, embodiments concern cartilage repair, such as articular cartilage repair. More particularly, embodiments for the disclosure concern using gene therapy for the attraction, generation and/or regeneration of chondrocytes or other cartilage-type cells and/or the generation and/or repair of cartilage tissue. In specific embodiments of the disclosure, gene therapy is provided that is capable of attracting and/or generating desired cells in vivo. In particular cases, gene therapy is employed for the attraction of fibroblasts that directly or indirectly are stimulated to differentiate into chondrocytes or chondrocyte-like cells or cartilage-type cells. In certain embodiments, fibroblasts in a joint or other type(s) of cells in a joint are present in the joint upon delivery of one or more gene therapy compositions to the joint and, following the delivery, the fibroblasts or one or more other types of cells differentiate into chondrocytes or chondrocyte-like cells or cartilage-type cells. In some cases, the delivery of one or more gene therapy compositions in a joint (such as among the presence of dying chondrocytes in a joint) act as a catalyst for differentiation of one or more types of cells in the joint to regenerate chondrocytes and/or cartilage-type cells or other cells that result at least in part in the same functionality that cartilage cells possess. In certain aspects, the delivery of one or more gene therapy compositions in the presence of dying chondrocytes in a joint act as a catalyst for generation of connective tissue in the joint, including generation of cartilage tissue. In some cases, one or more molecules from a dying chondrocyte are employed in the differentiation of one or more types of cells in a joint to chondrocytes, and such differentiation may or may not utilize gene products from one or more gene therapy composition(s). Embodiments of the invention concern all forms of cartilage and any other cells that may form and function in a location as if they were cartilage; in specific aspects, scar tissue is generated by methods of the invention. In particular cases wherein scar tissue is generated, that scar tissue acts as a cushion in the joint.

In some cases, gene therapy composition(s) are uptaken by one or more types of cells that already reside in vivo in a joint, although in other cases gene therapy composition(s) are uptaken by cells that are delivered to the joint and/or that already reside in the joint. The cells that are delivered to the joint may be differentiated prior to delivery to the joint or following delivery to the joint, and the gene therapy composition(s) may be exposed to the cells that are delivered to the joint prior to delivery to the joint or following delivery to the joint. Differentiation of cells into chondrocytes or chondrocyte-like cells may occur in any suitable manner in accordance with the disclosure, including, for example, differentiation of cells in vitro prior to implantation of the gene therapy into an individual or differentiation in vitro prior to implantation of the gene therapy into an individual and also in vivo following implantation. The cells that differentiate into chondrocytes or chondrocyte-like cells may be of any particular kind, but in specific embodiments the cells that differentiate into chondrocytes or chondrocyte-like cells are fibroblasts. In some embodiments, fibroblasts, adipose cells, stem cells, stem cells derived from fibroblast and/or mesenchymal stem cells are employed in any method of the invention.

The fibroblasts may differentiate into chondrocytes or chondrocyte-like cells prior to, during, and/or after exposure to the one or more gene therapy compositions. In particular aspects, fibroblasts are exposed to mechanical strain in vivo or in vitro prior to in vivo delivery and are also exposed to one or more gene therapy compositions. In cases wherein the gene therapy compositions are delivered to a joint, pressure on the joint may act as mechanical strain to cause, at least in part, differentiation of cells, including stem cells and/or fibroblasts.

In aspects of the disclosure, chondrocytes or chondrocyte-like cells or cartilage-type are produced for the purpose of cartilage regeneration and/or repair. Any gene or combination of genes may be employed for the purposes of the disclosure. For example, COL11A2, or others, may be employed for chondrocyte generation, cartilage-type cell generation and/or cartilage regeneration and/or repair. In certain embodiments, TGF-beta and FGF-2 are utilized in cartilage regeneration. In specific aspects, COL11A2, TGF-beta and/or FGF-2 are employed for in vivo cartilage generation from surrounding fibroblasts. In some cases, other genes referred to herein are utilized in compositions and methods of the invention.

Embodiments concern a therapeutic delivery (such as by injection, intravenous therapy (IV), oral ingestion, vascular placement, such as an angiogram, or even a topical approach) of certain gene(s), such as collagen-formation gene(s), including with or without a nutrient matrix and/or vessel. More specifically, but not exclusively, embodiments relate to methods and/or compositions for biological repair of cartilage using a delivery of cartilage-forming genes and/or a gene mixture that will attract surrounding fibroblasts to begin repair of the cartilage. This therapy acts as an in vivo workstation for cartilage restoration, in particular embodiments. In certain aspects, there is cartilage generation initiated in vitro, such as by using autologous chondrocytes and/or allogenic chondrocytes and/or fibroblasts, such as dermal fibroblasts. This mixture may be delivered (such as by injection) into one or more joints or in the vicinity of one or more joints, and this will attract other non-captured fibroblasts (for example) into the cartilage regeneration process, in particular embodiments. In certain embodiments, a matrix or scaffold may be introduced and then seeded either in vitro or in vivo with the gene therapy composition, fibroblasts, and/or chondrocytes to provide structure to the cartilage regeneration process.

The introduction of genes that aid in the production of cartilage attract fibroblasts or other suitable cells in the area of the cartilage undergoing degradation to differentiate into chondrocytes or chondrocyte-like cells for the purpose of replenishing and/or halting the cartilage degradation, in aspects of the disclosure. Because cartilage typically has low blood flow and access to nutrients, it is considered a difficult tissue in the body to regenerate. For this reason, in some aspects other elements besides the gene may be added to the therapeutic gene composition(s). For example, regulatory elements suitable for activity in a joint may be employed in the invention. In certain aspects, the composition comprises nutrients, and in particular aspects the composition Ahas an absorbable reservoir comprising oxygen and/or nutrients. In specific aspects, proteins/amino acids, phosphates, calcium, sodium, lipids, iron, sugars/starches, and/or vitamins may be utilized in one or more methods of the invention.

In particular embodiments, the gene therapy composition(s) comprises an expression vector. Any suitable expression vector may be utilized, but in some cases the expression vector is suitable for activity in a joint, including in avascular, aneural, and/or low oxygen environment. In specific cases, the expression vector comprises a promoter that is active in an avascular, aneural, and/or low oxygen environment.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention. The present application refers to a number of references and documents all of which are incorporated herein in their entirety.

DETAILED DESCRIPTION OF THE INVENTION

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the invention may "consist essentially of" or "consist of" one or more sequences of the invention, for example. Some embodiments of the invention may consist of or consist essentially of one or more elements, method steps, and/or methods of the invention. It is contemplated that any method or composition described herein can be implemented with respect to any other method or composition described herein.

I. Definitions

The term "cartilage-type cell" as used herein refers to any cell that could exist and function in the same capacity as a cartilage cell.

The term "chondrocyte-like cells" as used herein refers to cells that are not primary chondrocytes but are derived from stem cells (such as mesenchymal stem cells) or cells from other lineages (such as fibroblasts). These chondrocyte-like cells have a phenotype of chondrocytes (cells of cartilage). This means that not only do they have a shape of chondrocytes (polygonal and/or rhomboidal cells, for example), but also in certain cases at least they are able to aggregate and produce cartilage matrix components, such as sulfated proteoglycan and type II collagen, for example. Thus, exemplary markers of chondrocyte-like cells include one or more of aggrecan, which is a chondroitin sulfate and keratan sulfate proteoglycan, type II collagen, Sox-9 protein, cartilage link protein, and perlecan, which is a heparan sulfate proteoglycan, for example.

The term "hypoxia" as used herein refers to a deficiency in oxygen. In specific aspects, it refers to oxygen tension that is less than about 20%.

The term "joint" as used herein refers to a region in the body wherein two bones of a skeleton join.

The term "regeneration" as used herein is defined as a process that restores the normal functions of injured articular cartilage, and in at least certain cases also results in the formation of new tissue that is indistinguishable from the native cartilage.

The term "seeding" as used herein refers to implanting cells in a scaffold. The cells will attach to the scaffold and then grow and differentiate in the scaffold.

As used herein, the term "scaffold" is a mechanical unit upon which a matrix of cells could form.

As used herein, the term "matrix" would be a geometric shape that would then provide strength and structure.

II. General Embodiments

The present invention is directed to systems, methods, and compositions for treatment of an individual in need thereof, including treatment of an individual in need of cartilage repair. The present invention concerns methods and compositions for biological repair of any kind of cartilage, including intervertebral and joint cartilage, for example. In particular aspects, the present invention concerns the fields of cartilage repair, such as articular cartilage repair.

In certain aspects, the invention generates natural tissue in vivo (or in vitro or in vitro and in vivo), such as from fibroblasts, for example. More particularly, but not exclusively, the present invention relates to a method for growing and differentiating human fibroblasts into chondrocyte-like cells, for example. The cells may be autologous or allogeneic or a mixture thereof, in certain embodiments.

In specific embodiments, the invention employs differentiation of certain cells into chondrocyte-like cells. In specific embodiments, human dermal fibroblasts (HDFs), for example, are differentiated into chondrocyte-like cells under particular conditions employing gene therapy with one or more genes. Differentiation of cells into chondrocytes or chondrocyte-like cells may occur in any suitable manner, including in vivo following implantation or in vivo with naturally-residing cells, including fibroblasts.

In specific embodiments the invention provides a method for in vivo regeneration of a joint, such as an intervertebral disc, elbow, knee, shoulder, hip, temporo-mandibular joint, ankle, metatarsal, metacarpal and so forth.

It is an exemplary object of the present disclosure to provide a method to repair a joint, such as a degenerated intervertebral disc, e.g. restore intervertebral disc anatomy and improve its functioning. In particular aspects of the invention, there is provided a method to repair damaged disc. In one embodiment of the invention, there is a method of repairing damaged cartilage in a joint (such as an intervertebral disc) of an individual, comprising delivering fibroblasts subjected to gene therapy in accordance with the invention to the respective joint (such as intervertebral disc) of the individual or providing in vivo fibroblasts or other cells (including dying chondrocytes) with gene therapy. In specific embodiments of the invention, the gene therapy composition(s) or fibroblasts and the gene therapy composition(s) are delivered to a joint; in specific embodiments for the intervertebral disc, the gene therapy composition(s) or fibroblasts and the gene therapy composition(s) are delivered in the absence of removing part or all of the degenerated disk.

In certain aspects of the invention, an individual is provided another therapy in addition to the methods of the invention. For example, before, during, and/or after delivery of the gene therapy composition(s) or the gene therapy composition(s) and the fibroblast cells, the individual may receive one or more drugs. Exemplary additional therapies include antibiotics, Non Steroidal Anti-Inflammatory Drugs (NSAIDs), simple pain killers (analgesics), muscle relaxants, and/or functional rehabilitation as needed. In specific embodiments, the individual may be provided one or more of an antibiotic, antifungal agent, antiviral agent, nutrient injection, IV, or oral tablet.

In certain aspects of the invention, the cells differentiate into chondrocyte cells or chondrocyte-like cells, such as wherein the chondrocyte cells or chondrocyte-like cells secrete a molecule selected from the group consisting of aggrecan, type II collagen, Sox-9 protein, cartilage link protein, perlecan, and combinations thereof. In particular cases, the cells are differentiated from fibroblast cells, and exemplary fibroblast cells include dermal fibroblasts, tendon fibroblasts, ligament fibroblasts, synovial fibroblasts, foreskin fibroblasts, or a mixture thereof.

In specific embodiments, there may or may not be growth factors provided to the individual, including growth factors such as bone morphogenetic protein 2 (BMP-2), BMP-4, BMP-6, BMP-7, cartilage-derived morphogenetic protein (CDMP), transforming growth factor beta (TGF-β), insulin growth factor one (IGF-I), fibroblast growth factors (FGFs), basic fibroblast growth factor (bFGF), FGF-2, platelet-derived growth factor (PDGF), and a mixture thereof. The delivery of the growth factors may be upon, before, and/or after delivery of the gene therapy composition(s). In cases wherein there is cell manipulation outside the body followed by delivery of the cells, one or more growth factors may be provided at the time of delivery of the cells.

In a further embodiment, there is a kit comprising one or more gene therapy composition(s) and may also include certain cells, such as fibroblasts, wherein any component of the kit is housed in one or more suitable containers. In specific embodiments, the kit further comprises one or more reagents suitable for enhancing in vivo differentiation from fibroblasts to chondrocytes or chondrocyte-like cells. In some embodiments, the kit of the invention includes one or more apparatuses for delivery of gene therapy composition(s) and/or fibroblasts to an individual.

In some embodiments of the invention, there are methods and compositions related to delivering gene therapy composition(s) and/or fibroblasts to a site in vivo in an individual in need thereof. In specific embodiments, the site is in vivo and in need of chondrocytes, including in need of cartilage. For example, a site in need of chondrocytes includes joints, for example cartilaginous joints (e.g., vertebrae). In some embodiments, the fibroblasts are obtained from the individual in need of cartilage. In specific embodiments, fibroblasts are delivered to at least one intervertebral disc in an individual.

In particular cases, the gene therapy composition(s) are delivered to the joint. In some cases the gene therapy composition(s) are delivered between invertebral discs. In certain cases, the gene therapy composition(s) are delivered between or in nucleus pulposus and fissures in the inner annulus fibrosus. The gene therapy composition(s) may be delivered between invertebral discs, including nucleus pulposus and fissures in the inner annulus fibrosus, for example.

In some embodiments, there is a method of producing fibrous tissue and/or chondrocytic tissue in a joint of an individual, comprising the step of delivering one or more gene therapy compositions to the joint of the individual.

In particular embodiments, one or more gene therapy composition(s) are delivered in vivo to a joint and resident cells in the joint uptake the composition(s). In certain embodiments, however, cells are provided to the joint before, during and/or after delivery of the one or more gene therapy composition(s). In such cases, any cell may be employed so long as the cell is capable of differentiating into a chondrocyte or chondrocyte-like cell. However, in specific embodiments, the cell is a fibroblast cell, such as a dermal fibroblast, tendon fibroblast, ligament fibroblast, or synovial fibroblast, for example. Autologous cells may be utilized, although in alternative embodiments allogeneic cells are employed; in specific embodiments, the allogeneic cells have been assayed for disease and are considered suitable for human transmission. In certain aspects of the invention, the cell or cells are autologous, although in alternative embodiments the cells are allogeneic. In cases wherein the cells are not autologous, prior to use in the invention the cells may be processed by standard means in the art to remove potentially hazardous materials, pathogens, etc.

III. Therapeutic Genes

In embodiments of the invention, one or more genes are used as therapeutic compositions. The compositions may be employed to facilitate differentiation of fibroblasts to chondrocytes or chondrocyte-like cells or may be employed to enhance the level of a gene product from the therapeutic composition once a fibroblast has differentiated to a chondrocyte or chondrocyte-like cell. In some cases, the one or more provided genes work in conjunction with molecules present in an joint from dying chondrocytes to facilitate generation of chondrocytes or chondrocyte-type cells or cartilage tissue in the joint.

In particular aspects, polynucleotides encompassing the one or more therapeutic genes comprise the full-length genes, although in some aspects, a fragment of a gene is utilized, although the fragment still has therapeutic activity or encodes a peptide or polypeptide that has therapeutic activity. The genes may be mammalian in nature, including human, mouse, rat, and so forth.

In particular aspects, the one or more therapeutic genes are a collagen formation gene (including of any type), a cartilage formation gene, a connective tissue formation gene, a transcription factor, a cartilage matrix gene, a receptor gene, or a signaling molecule, for example. In specific embodiments, the one or more therapeutic genes are not a member of the transforming growth factor (TGF) beta superfamily.

In specific embodiments, the gene therapy composition encodes one or more matrix molecules, such as collagen I, collagen II, proteoglycan, or a combination thereof. In specific embodiments, the collagen comprises type I and type II collagen. In some cases, one of the proteoglycans is aggrecans.

In specific embodiments, one or more of the following genes are employed in the invention: COL1A1, COL1A2, COL2A1, COL3A1, COL4A1, COL4A2, COL4A3, COL4A4, COL4A5, COL4A6, COL5A1, COL5A2, COL5A3, COL6A1, COL6A2, COL6A3, COL6A4, COL6A5, COL7A1, COL8A1, COL8A2, COL9A1, COL9A2, COL9A3, COL10A1, COL11A1, COL11A2, COL12A1, COL13A1, COL14A1, COL15A1, COL16A1, COL17A1, COL18A1, COL19A1, COL20A1, COL21A1, COL22A1, COL23A1, COL24A1, COL25A1, COL26A1, COL27A1, and COL28A1.

Exemplary genes include cartilage matrix genes, such as proteoglycans and COL2, -9, -10, and -11; receptor genes [fibroblast growth factor 2 (FGFR2); parathyroid hormone-related peptide receptor (PTHrP-R)]; one or more transcription factors (SOX5, -6, and -9); SOX4; vascular endothelial growth factor (VEGF); matrix metalloproteinase 14 (MMP14); forkhead; CD10; MMP13; collagens (such as COL3A1 and COL16A1); signaling molecule (WNT11); a homeobox homolog (BAPX1); a receptor (IL-1R1); an IGFs modulator (IGFBP5); and/or a mettaloproteinase (MMP16) (see Sekiya et al., 2002). In certain aspects, the following genes may be employed: known markers of chondrogenic capacity (collagen II, FGFR3, BMP2, ALK1), anabolic growth factors (BMP5 and IGF1) or matrix-degrading enzymes (MMP13 and ADAMTS5) (see Hellingman et al., 2011).

In particular aspects, one or more of the following are utilized: GREM1, BMP6, COL10A1, or MMP13 (see Funari et al., 2007). BMC Genomics 2007, 8:165 In specific aspects, one may employ one or more of the following: COL11A1, BCL10, MCOLN2, LRRC8C, PTGFR, RLF, COL9A2, MATN1, PDPN, TNFRSF18, ITGA10, THBS3, SCYL1BP1, KCNT2, 244533_at, ARF1, 222348_at, SLC4A5, HSPC159, RHOQ, MATN3, SULT1C2, 236289_at, BCL2L11, FLJ16008, KLF7, NRP2, SER-PINE2, FN1, B3GNT7, ADAMTS9, ANKRD28, GAL-NTL2, IRAK2, SETD5, FNDC3B, B3GNT5, CYTL1, IBSP, 229221_at, COL25A1, PET112L, EDNRA, 1563414_at, OSMR, C1QTNF3, ZFYVE16, 225611_at, MAST4, EDIL3, 230204_at, 230895_at, HAPLN1, PDLIM4, cr5q35 SQSTM1, COL11A2, SCUBE3, CMAH, 236685_at, BMP6, COL9A1, COL10A1, ULBP2, LRP11, SOD2, SYNJ2, WTAP, HIG2, KIAA1718, FAM62B, UBE3C, TNFRSF10D, SLC25A37, ChGn, RB1CC1, C8orf72, EIF2C2, HAS2, TRPS1, WISP1, 235821_at, PTK2, ZCCHC7, RPS6, GLIS3, SLC28A3, 1555841_at, MGC17337, EDG2, 229242_at, COL27A1, ITGB1, C10orf49, YME1L1, AKR1C2, CHST3, LOXL4, SFXN3, 228910_at, CD44, FOSL1, RELA, MMP12, MMP13, MMP3, KIAA0999, ASAM, LOC399959, ETNK1, SOX5, CHST11, ATF1, SRGAP1, DSPG3, LOC338758, KIAA0701, SLC41A2, RHOF, FZD10, NUPL1, USP12, UFM1, LECT1, GPC6, ERO1L, BDKRB1, SEMA6D, LACTB, ARIH1, CSPG4, AGC1, LOC283824, VASN, WWP2, NOS2A, LOC201181, MSI2, PITPNC1, TGIF, 1552288_at, 1552289_a_at, ZNF146, RELB, MIA, ZNF160, SNX5, BMP2, RNF24, HSUP1, MATN4, BIC, RUNX1, LIF, RP4-756G23.1, RPS6KA3, TNMD, RP6-213H19.1 (see Funari et al., 2007).

Although in specific embodiments a member of the TGF β superfamily is not employed in the invention, in alternative embodiments one or more members of the TGF beta superfamily is utilized including TGF β, TGF-β3, TGF-β2, TGF-β4, TGF-β1, TGF-β5 (Xenopus), BMP-2, BMP-4, Drosophila DPP, BMP-5, BMP-6, Vgr1, OP-1/BMP-7, Drosophila 60A, GDF-1, Xenopus Vgf, BMP-3, Inhibin-βA, Inhibin-βB, Inhibin-α, and MIS (see U.S. Pat. No. 7,338, 655, incorporated by reference herein in its entirety).

In specific embodiments, part or all of a gene is utilized in embodiments of the methods and/or compositions. All or part of a coding region for a gene may be employed, and one or more regulatory regions for a particular gene may be utilized. In specific embodiments, one may utilize a fragment of a gene, including a fragment of a coding region, and the fragment will still retain therapeutic activity. In specific cases, a wild-type sequence of a particular gene is utilized, and the skilled artisan recognizes that the sequence for a gene may be identified in a variety of databases, such as the National Center for Biotechnology Information's Gen-Bank® database. In particular cases, the sequence utilized in the polynucleotide compositions is not identical to a wild-type sequence but differs from the sequence in one or more nucleotides or in one or more amino acids of the encoded gene product. The sequence utilized in the composition may be 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, and so forth, identical to a corresponding wild-type DNA sequence or such percentage identical to the encoded gene product when compared to the polypeptide sequence of the encoded wild-type polypeptide.

IV. Gene Therapy Embodiments

Embodiments include employing one or more polynucleotides capable of encoding a therapeutic gene product for chondrocyte regeneration, cartilage generation, and/or cartilage repair. In particular embodiments, the gene product is utilized by a fibroblast or other type of cell in a joint to facilitate differentiation of the fibroblast to chondrocytes or chondrocyte-like cells and/or is utilized by a chondrocyte or chondrocyte-like cell that differentiated from a fibroblast, stem cell, or adipose cell.

The polynucleotide may or may not encode an entire gene product. In cases wherein less than the entire gene product is encoded, the fragment is nevertheless biologically active and capable of having activity for chondrocyte generation and/or cartilage repair and/or cartilage regeneration. In some cases, expression vectors that comprise the therapeutic gene product or biologically active fragment thereof comprise a selectable marker.

A further embodiment of the present invention includes employing a polynucleotide capable of encoding a therapeutic gene product or a biologically active derivative or fragment thereof, and employing as the expression vector any vector known to one of ordinary skill in the art capable of stable maintenance within the targeted cell or tissue upon delivery, regardless of the method of delivery utilized. One such method is the direct delivery of the vector molecule, whether it be a viral or non-viral vector molecule, to the target cell or tissue.

Another embodiment of this invention provides a method for introducing at least one gene encoding a product into at least one cell for use in treating the mammalian host. This method includes employing viral or non-viral means (including plasmids) for introducing the gene coding for the product into the desired cell. More specifically, certain methods include a liposome encapsulation, calcium phosphate coprecipitation, electroporation, or DEAE-dextran mediation, and includes employing as the gene a gene capable of encoding a member of a therapeutic gene product or biologically active derivative or fragment thereof, and optionally a selectable marker.

Another embodiment of this invention provides a method for introducing at least one gene encoding a product into at least one desired cell for use in treating a mammalian host. This method includes employing the biologic means of utilizing a virus or other means to deliver a vector molecule to a target cell or tissue. Preferably, the virus is a pseudo-virus, the genome having been altered such that the pseudovirus is capable only of delivery and stable maintenance within the target cell, but not retaining an ability to replicate within the target cell or tissue. The altered viral genome is further manipulated by recombinant DNA techniques such that the viral genome acts as a DNA vector molecule which contains the heterologous gene of interest to be expressed within the target cell or tissue. The viral vector may be retroviral vector, adenoviral vector, lentiviral vector, or adeno-associated viral vector, for example.

An embodiment of the invention is a method of delivering a desired therapeutic gene product to a target joint space by delivering a polynucleotide that encodes the product to a desired location of a mammalian host. For example, a DNA sequence of interest encoding a part or all of a therapeutic gene product is subcloned into a vector of choice, the recombinant vector is then used to infect in vitro-cultured desired cells, and the transduced connective tissue cells, such as autografted cells, are transplanted into a location of interest, such as by intra-articular injection; in alternative embodiments, the recombinant vector is delivered to a location of interest in vivo, wherein the vector infects in vivo cells, such as in vivo fibroblasts in a joint, for example.

A method of the present invention involves direct in vivo delivery of a therapeutic gene to the desired tissue of a mammalian host through use of either an adenovirus vector, adeno-associated virus (AAV) vector or herpes-simplex virus (HSV) vector. In other words, a DNA sequence of interest encoding a functional protein or protein fragment is subcloned into the respective viral vector. The gene product-containing viral vector is then grown to adequate titer and directed into the desired space, preferably by intra-articular injection.

Direct intra-articular injection of a DNA molecule containing the gene of interest into a joint results in transfection of the recipient connective tissue cells (including fibroblasts at the site) and hence bypasses the requirement of removal, in vitro culturing, transfection, selection, as well as transplanting the vector containing-fibroblast to promote stable expression of the heterologous gene of interest.

Methods of presenting the DNA molecule to target cells in a joint includes, but is not limited to, encapsulation of the DNA molecule into cationic liposomes, subcloning the DNA sequence of interest in a retroviral or plasmid vector, or the direct injection of the DNA molecule itself into the joint. The DNA molecule, regardless of the form of presentation to the joint, is preferably presented as a DNA vector molecule, either as recombinant viral DNA vector molecule or a recombinant DNA plasmid vector molecule. Expression of the heterologous gene of interest is ensured by inserting a promoter fragment active in eukaryotic cells directly upstream of the coding region of the heterologous gene. One of ordinary skill in the art may utilize known strategies and techniques of vector construction to ensure appropriate levels of expression subsequent to entry of the DNA molecule into the connective tissue.

In a preferred embodiment, fibroblasts recovered from a joint are cultured in vitro for subsequent utilization as a delivery system for gene therapy. It will be apparent that Applicants are not limited to the use of the specific connective tissue disclosed. It would be possible to utilize other tissue sources for in vitro culture techniques. The method of using the gene of this invention may be employed both prophylactically and in the therapeutic treatment. One may utilize the teachings herein either prophylactically or therapeutically to treat any susceptible or affected joint.

In another embodiment of this invention, a compound for parenteral administration to a patient in a therapeutically effective amount is provided that contains a gene encoding a TGF-.beta. superfamily protein and a suitable pharmaceutical carrier.

Another embodiment of this invention provides for a compound for parenteral administration to a patient in a prophylactically effective amount that includes a gene encoding a TGF-beta superfamily protein and a suitable pharmaceutical carrier.

A further embodiment of this invention includes the method as hereinbefore described including introducing the gene into the cell in vitro. This method also includes subsequently transplanting the infected cell into the mammalian host. This method includes after effecting the transfecting of the connective tissue cell but before the transplanting of the infected cell into the mammalian host, storing the transfected connective tissue cell. It will be appreciated by those skilled in the art that the infected connective tissue cell may be stored frozen in 10 percent DMSO in liquid nitrogen, for example. Embodiments include employing a method to substantially prevent the development of joint disease or injury in a mammalian host having a high susceptibility of developing joint disease or injury.

Another embodiment of this invention includes a method of introducing at least one gene encoding a product into at least one cell of a connective tissue of a mammalian host for use in treating the mammalian host as hereinbefore described including effecting in vivo the infection of the cell by introducing the viral vector containing the gene coding for the product directly into the mammalian host. Preferably, this method includes effecting the direct introduction into the mammalian host by intra-articular injection. Methods include employing the method on a mammalian host for therapeutic use. Further this method also includes employing the method to repair and regenerate the connective tissue as hereinbefore defined.

It will be appreciated by those skilled in the art, that the viral vectors employing a liposome are not limited by cell division as is required for the retroviruses to effect infection and integration of connective tissue cells. This method employing non-viral means as hereinbefore described includes employing as the gene a gene capable of encoding a member belonging to the TGF-β superfamily and a selectable marker gene, such as an antibiotic resistance gene.

Another embodiment of the present invention is delivery of a DNA sequence encoding a member of the TGF-β superfamily to the connective tissue of a mammalian host by any of the methods disclosed within this specification so as to effect in vivo expression of collagen to regenerate connective tissue, such as cartilage.

In a specific method disclosed as an example, and not as a limitation to the present invention, a DNA plasmid vector containing the TGF-β coding sequence was ligated downstream of the metallothionein promoter.

V. Nucleic Acid-Based Expression Systems

A. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

a. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB on the world wide web) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

The identity of tissue-specific promoters or elements, as well as assays to characterize their activity, is well known to those of skill in the art. Nonlimiting examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), and human platelet endothelial cell adhesion molecule-1 (Almendro et al., 1996).

b. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/ enhancer to transcribe a single message (see U.S. Pat. Nos. 5,925,565 and 5,935,819, each herein incorporated by reference).

c. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

e. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

f. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

g. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

h. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

i. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, *E. coli* LE392.

Further useful plasmid vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Bacterial host cells, for example, *E. coli*, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

j. Viral Vectors

The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Non-limiting examples of virus vectors that may be used to deliver a nucleic acid of the present invention are described below.

1. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992).

2. AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno-associated virus (AAV) is an attractive vector system for use in embodiments of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

3. Retroviral Vectors

Retroviruses have use as delivery vectors due to their ability to integrate their genes into the host genome, transferring a large amount of foreign genetic material, infecting a broad spectrum of species and cell types and of being packaged in special cell-lines (Miller, 1992).

In order to construct a retroviral vector, a nucleic acid is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

4. Other Viral Vectors

Other viral vectors may be employed as constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

5. Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

B. Vector Delivery and Cell Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789, 215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322, 783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by Agrobacterium-mediated transformation (U.S. Pat. Nos. 5,591,616 and 5,563,055, each incorporated herein by reference); by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

a. Ex Vivo Transformation

Methods for transfecting cells and tissues removed from an organism in an ex vivo setting are known to those of skill in the art. For example, canine endothelial cells have been genetically altered by retroviral gene transfer in vitro and transplanted into a canine (Wilson et al., 1989). In another example, yucatan minipig endothelial cells were transfected by retrovirus in vitro and transplanted into an artery using a double-balloon catheter (Nabel et al., 1989). Thus, it is contemplated that cells or tissues may be removed and transfected ex vivo using the nucleic acids of the present invention. In particular aspects, the transplanted cells or tissues may be placed into an organism. In preferred facets, a nucleic acid is expressed in the transplanted cells or tissues.

b. Injection

In certain embodiments, a nucleic acid may be delivered to an organelle, a cell, a tissue or an organism via one or more injections (i.e., a needle injection), such as, for example, subcutaneously, intradermally, intramuscularly, intravenously, intraperitoneally, etc. Methods of injection of compositions are well known to those of ordinary skill in the art (e.g., injection of a composition comprising a saline solution). Further embodiments of the present invention include the introduction of a nucleic acid by direct microinjection. Direct microinjection has been used to introduce nucleic acid constructs into Xenopus oocytes (Harland and Weintraub, 1985). The amount of composition used may vary upon the nature of the gene product or gene as well as the organelle, cell, tissue or organism used.

c. Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

d. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

e. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

f. Sonication Loading

Additional embodiments of the present invention include the introduction of a nucleic acid by direct sonic loading. LTK⁻ fibroblasts have been transfected with the thymidine kinase gene by sonication loading (Fechheimer et al., 1987).

g. Liposome-Mediated Transfection

In a further embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

h. Receptor Mediated Transfection

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

i. Microprojectile Bombardment

Microprojectile bombardment techniques can be used to introduce a nucleic acid into at least one, organelle, cell, tissue or organism (U.S. Pat. Nos. 5,550,318; 5,538,880; 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

Microprojectile bombardment may be used to transform various cell(s), tissue(s) or organism(s), such as for example any plant species. Examples of species which have been transformed by microprojectile bombardment include monocot species such as maize (PCT Application WO 95/06128), barley (Ritala et al., 1994; Hensgens et al., 1993), wheat (U.S. Pat. No. 5,563,055, incorporated herein by reference), rice (Hensgens et al., 1993), oat (Torbet et al., 1995; Torbet et al., 1998), rye (Hensgens et al., 1993), sugarcane (Bower et al., 1992), and sorghum (Casas et al., 1993; Hagio et al., 1991); as well as a number of dicots including tobacco (Tomes et al., 1990; Buising and Benbow, 1994), soybean (U.S. Pat. No. 5,322,783, incorporated herein by reference), sunflower (Knittel et al. 1994), peanut (Singsit et al., 1997), cotton (McCabe and Martinell, 1993), tomato (VanEck et al. 1995), and legumes in general (U.S. Pat. No. 5,563,055, incorporated herein by reference).

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into a cell (e.g., a plant cell) by acceleration is the Biolistics Particle Delivery System, which can be used to propel particles coated with DNA or cells through a screen, such as a stainless steel or Nytex screen, onto a filter surface covered with cells, such as for example, a monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

C. Host Cells

In some embodiments, host cells are employed in generation of one or more gene therapy compositions. As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid.

In certain embodiments, it is contemplated that RNAs or proteinaceous sequences may be co-expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for RNAs, which could then be expressed in host cells transfected with the single vector.

A tissue may comprise a host cell or cells to be transformed with a composition of the invention. The tissue may be part or separated from an organism. In certain embodiments, a tissue may comprise, but is not limited to, adipocytes, alveolar, ameloblasts, axon, basal cells, blood (e.g., lymphocytes), blood vessel, bone, bone marrow, brain, breast, cartilage, cervix, colon, cornea, embryonic, endometrium, endothelial, epithelial, esophagus, facia, fibroblast, follicular, ganglion cells, glial cells, goblet cells, kidney, liver, lung, lymph node, muscle, neuron, ovaries, pancreas, peripheral blood, prostate, skin, skin, small intestine, spleen, stem cells, stomach, testes, anthers, ascite tissue, cobs, ears, flowers, husks, kernels, leaves, meristematic cells, pollen, root tips, roots, silk, stalks, and all cancers thereof.

In certain embodiments, the host cell or tissue may be comprised in at least one organism. In certain embodiments, the organism may be, but is not limited to, a prokayote (e.g., a eubacteria, an archaea) or an eukaryote, as would be understood by one of ordinary skill in the art (see, for example, webpage http://phylogeny.arizona.edu/tree/phylogeny.html).

Numerous cell lines and cultures are available for use as a host cell, and they can be obtained through the American Type Culture Collection (ATCC), which is an organization that serves as an archive for living cultures and genetic materials (on the world wide web). An appropriate host can be determined by one of skill in the art based on the vector backbone and the desired result. A plasmid or cosmid, for example, can be introduced into a prokaryote host cell for replication of many vectors. Cell types available for vector replication and/or expression include, but are not limited to, bacteria, such as *E. coli* (e.g., *E. coli* strain RR1, *E. coli* LE392, *E. coli* B, *E. coli* X 1776 (ATCC No. 31537) as well as *E. coli* W3110 (F-, lambda-, prototrophic, ATCC No. 273325), DH5α, JM109, and KC8, bacilli such as *Bacillus subtilis*; and other enterobacteriaceae such as *Salmonella typhimurium, Serratia marcescens*, various *Pseudomonas* specie, as well as a number of commercially available bacterial hosts such as SURE® Competent Cells and Solopack™ Gold Cells (Stratagene®, La Jolla). In certain embodiments, bacterial cells such as *E. coli* LE392 are particularly contemplated as host cells for phage viruses.

Examples of eukaryotic host cells for replication and/or expression of a vector include, but are not limited to, HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

D. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

It is contemplated that the proteins, polypeptides or peptides produced by the methods of the invention may be "overexpressed", i.e., expressed in increased levels relative to its natural expression in cells. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein, polypeptide or peptide in comparison to the level in natural cells is indicative of overexpression, as is a relative abundance of the specific protein, polypeptides or peptides in relation to the other proteins produced by the host cell and, e.g., visible on a gel.

In some embodiments, the expressed proteinaceous sequence forms an inclusion body in the host cell, the host cells are lysed, for example, by disruption in a cell homogenizer, washed and/or centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed. Inclusion bodies may be solubilized in solutions containing high concentrations of urea (e.g. 8M) or chaotropic agents such as guanidine hydrochloride in the presence of reducing agents, such as β-mercaptoethanol or DTT (dithiothreitol), and refolded into a more desirable conformation, as would be known to one of ordinary skill in the art.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Gene Therapy for the Regeneration of Chondrocytes or Cartilage Type Cells

An individual in need of regeneration of chondrocytes or cartilage-type cells is the subject of one or more methods of the disclosure and/or exposed to one or more compositions of the disclosure. The individual may be at risk for being in need of regeneration of chondrocytes or cartilage type cells, or the individual may be diagnosed as needing regeneration of chondrocytes or cartilage type cells. An individual being at risk for needing regeneration of chondrocytes or cartilage type cells may be at risk for any reason, including by being or having been an athlete, by having a joint injury, obese individuals, those whose occupations or lifestyle require physical labor, including excessive lifting, or by being susceptible to having a medical condition that deleteriously affects joints or cartilage (such as with a family history or having one or more known markers and/or risk factors for susceptibility to the medical condition, for example), those who exercise for health reasons, or as a result of trauma. An individual known to need regeneration of chondrocytes or cartilage type cells includes an individual with a medical condition that deleteriously affects joints or cartilage. Exemplary medical conditions include intervertebral disc disease, chondrodystrophies, including osteoarthritis, achondroplasia, costochondritis, spinal disc herniation, and so forth.

A joint of an individual in need of repair or prevention of repair is provided one or more gene therapy composition(s). The gene therapy composition(s) may be provided to the joint of the individual with or without a second component, such as a plurality of cells, for example, and/or reservoir (such as an absorbable reservoir) comprising oxygen and/or nutrients; one or more drugs may also be provided. In some embodiments, scaffolding laced with gene therapy and nutrients is provided.

Upon delivery of the one or more gene therapy composition(s) to at least one joint, chondrocytes or chondrocyte-like cells or cartilage-type cells are generated in the respective joint, in some cases. Upon delivery of the one or more gene therapy composition(s) to at least one joint, cartilage tissue is regenerated, in some cases. The mechanism by which such results are produced from the gene therapy delivery may be from one or more of a variety of reasons, including 1) attraction of fibroblasts or other non-chondrocyte cells to a joint that then differentiate into chondrocytes or chondrocyte-like cells or cartilage-type cells; 2) differentiation of fibroblasts or other non-chondrocyte cells (including those residing in the joint) into chondrocytes or chondrocyte-like cells or cartilage-type cells; 3) a combination of one or more gene therapy composition(s) with one or more molecules from a chondrocyte that is dying or present in dying tissue or tissue in need of repair; and/or 4) the resulting production of advantageous or mechanically sufficient scar tissue or fibrous scar tissue.

Example 2

Examples of Materials and Methods

In certain embodiments, the following methods are employed in the disclosure.

Procurement and Expansion of Human Wharton's Jelly Cells

Human Wharton's jelly cells (hWJCs) were isolated from Wharton's jelly of human umbilical (Devarajan et al., 2013) cords collected with informed (KU-IRB #15402) following our previously published protocol. hWJCs were cultured in traditional hWJC medium (10% fetal bovine serum (FBS-MSC Qualified) and 1% Penicillin-Streptomycin in low glucose DMEM (Life Technologies, Carlsbad, CA)). hWJCs medium was changed three times per week, and hWJCs were maintained at 37° C. with 5% $CO_2$ in a cell culture grade incubator. hWJCs were flash frozen at passage 2 (P2) until needed for experiments. hWJCs were thawed and expanded from P2 to P5, then used for experiments. All experiments were performed in triplicate for each cord.

Plasmid

The Sox9 gene (NCBI GenBank ID: NC_000017.11) was synthesized by Blue Heron Biotech LLC. (Bothel, WA), and cloned into a Dendra2-C plasmid (Clontech, Mountain View, CA) at the carboxyl end of the Dendra2 sequence. Dendra2 is a green-to-red photo-convertible fluorescent protein. The Dendra2 plasmid contains a cytomegalovirus (CMV) promoter to drive transcription of Dendra2 and any sequence fused to Dendra2. The Dendra2 plasmid additionally contains a Simian virus 40 (SV40) promoter to drive transcription of a kanamycin resistance cassette for bacterial selection and a neomycin resistance cassette for eukaryotic selection.

Experimental Design and Transfection hWJCs were treated with ROCK Inhibitor and transfected via a 4D-Nucleofector using program FF-104 according to previous published protocol. (Mellott et al., 2014) hWJCs were transfected at a concentration of $5 \times 10^5$ per reaction, and were transfected with 5 µg of pDNA. After transfection hWJCs were transferred to a 6-well plate (BD Biosciences, San Jose, CA) or Nunc™ Lab-Tek™ 8-well chambered coverglass slides (Thermo Scientific, Waltham, MA) pre-coated with Fibronectin (BD Biosciences) containing 1.5 mL or 0.5 mL, respectively, of pre-warmed 37° C. traditional hWJC medium with 10 μM of Y-27632 ROCK Inhibitor, and placed into a cell culture grade incubator at 37° C. with 5% $CO_2$.

Gene Expression

At 1 and 7 d after transfection, transfected cells and untreated controls were collected and harvested for gene expression analysis via real time quantitative polymerase chain reaction (RT-qPCR). Cells were analyzed for the chondrogenic genes, Sox9 and Collagen type II. Cycle threshold (Ct) values were recorded and analyzed via the Delta-Delta-Ct method. Values were normalized to day 0 untreated control samples and the endogenous controls. Three technical replicates from each umbilical cord were taken for gene expression analysis at 1 and 7 d post transfection.

Live Cell Fluorescent Imaging hWJCs were collected and stained with Hoechst 33342 dye (Life Technologies) for live cell imaging 24 h after transfection. hWJCs were imaged using a an Olympus IX81 inverted spinning disc confocal microscope base (Olympus America, Center Valley, PA). Images were captured using the acquisition and analysis software, SlideBook (Intelligent Imaging Innovations (3i), Denver, CO). A mercury arc lamp was used with the following excitation filters (Excitation/Emission) for image collection: Hoechst (387±11 nm/447±60 nm), GFP (494±20 nm/531±22 nm), and RFP (575±25 nm/624±40 nm). A montage was generated from 49 (seven by seven arrangement) neighboring fields of view that were aligned together to generate one comprehensive composite image of the sample.

Immunocytochemistry

At 1 and 7 d after transfection, transfected cells and controls were collected for immunocytochemistry. Cells were fixed by first washing cells in 37° C. PBS, followed by fixation with 4% formaldehyde in PBS for 15 min. Cells were then washed and incubated for 5 min with PBS three times. Afterward, cells were permeabilized with 0.25% Triton X-100 in PBS, then washed three times in PBS for 5 min. Cells were blocked with 4% bovine serum albumin (BSA) and 10% normal serum (from secondary antibody host) in PBS for 60 min. Afterward, cells were incubated with Sox9 (Abcam, Cambridge, MA) and Collagen type II (Abcam) primary antibodies overnight. The following day, cells were washed three times in PBS for 15 minutes each. Afterward, cells were incubated with Qdot conjugated secondary antibodies (Qdot 565 Mouse conjugate for Sox9 and Qdot 655 Rabbit for Collagen type II (Life Technologies)) over night. The following day, cells were washed three times in PBS for 15 minutes each. Cells were counterstained with Ethidium Monoazide Bromide (10 nM, Life Technologies) for 30 min, and then dehydrated with graded ethanol, followed by double exposure to 100% toluene. Cells were then mounted in Qmount™ Qdot® Mounting Media (Life Technologies). Cells were imaged using confocal microscopy using a 405 nm solid-state laser for Qdot excitation, a 488 nm solid-state laser for Ethidium Monoazide Bromide excitation, and the following emission filters: Ethidium Monoazide Bromide (531±22 nm), Qdot 565 (560±25 nm), and Qdot 655 (655±15 nm).

Statistical Analysis

All values are reported as statistical means with standard deviations, unless otherwise noted. A one-way ANOVA was performed with a post hoc Tukey's test to assess statistical significance with p set at ≤0.05, and power>0.8. The software SPPS (IBM) version 22 was used to compute all statistical analyses.

REFERENCES

Devarajan K, Forrest M L, Detamore M S, Staecker H. Adenovector-mediated gene delivery to human umbilical cord mesenchymal stromal cells induces inner ear cell phenotype. Cell Reprogram. 2013; 15(1):43-54. Epub 2013/02/06. doi: 10.1089/cell.2011.0097. PubMed PMID: 23379581.

Funari et al., Cartilage-selective genes identified in genome-scale analysis of non-cartilage and cartilage gene expression. 2007, BMC Genomics 2007, 8:165

Hellingman et al., Differences in cartilage-forming capacity of expanded human chondrocytes from ear and nose and their gene expression profiles. 2011 Cell Transplant. 2011; 20(6):925-40

Majumdar M K, Wang E and Morris E A. BMP-2 and BMP-9 promotes chondrogenic differentiation of human multipotential mesenchymal cells and overcomes the inhibitory effect of IL-1. J. Cell. Physiol. 2001(189):275-284.

Mellott A J, Godsey M E, Shinogle H E, Moore D S, Forrest M L, Detamore M S. Improving Viability and Transfection Efficiency with Human Umbilical Cord Wharton's Jelly Cells Through Use of a ROCK Inhibitor. Cell Reprogram. 2014. Epub 2014/02/21. doi: 10.1089/cell.2013.0069. PubMed PMID: 24552552.

Seppa, N. Cartilage creation. New joint tissue could keep people moving, reducing need for knee or hip replacements. Science News 2012 (189 #3):22.

Sekiya et al., 2002, Proc Natl Acad Sci USA. 2002 Apr. 2; 99(7): 4397-4402.

Zaslav K. Cole B. et al: *The American Journal of Sports Medicine.* 2009; 37(1):42-55.

Zaslav K. Cole B. et al. A Prospective Study of Autologous Chondrocyte Implantation in Patients Who Failed Prior Treatments for Articular Cartilage *The American Journal of Sports Medicine.* 2009; 37(1):42-55.

Zhang, Lijie, Jerry Hu, Kyriacos A. Athanasiou The Role of Tissue Engineering in Articular Cartilage Repair and Regeneration Crit Rev Biomed Eng. 2009; 37(1-2): 1-57.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of producing chondrocytes in a joint of an individual in need thereof to treat chondrodystrophies, comprising the step of delivering to the joint of an individual with a chondrodystrophy at least one expression vector encoding two or more therapeutic polynucleotides, wherein upon the delivering of the at least one expression vector, a fibroblast in the joint differentiates into a chondrocyte, wherein the two or more therapeutic polynucleotides comprise Sox9 and MMP3.

2. The method of claim 1, wherein the two or more therapeutic polynucleotides encode a full gene product or a biologically active fragment of a full gene product.

3. The method of claim 1, wherein the two or more therapeutic polynucleotides are present on at least one expression vector.

4. The method of claim 1, wherein the at least one expression vector is a viral vector or a non-viral vector.

5. The method of claim 4, wherein the non-viral vector is a plasmid.

6. The method of claim 4, wherein the viral vector is a lentiviral vector, adenoviral vector, adeno-associated viral vector, or retroviral vector.

7. The method of claim 1, wherein the two or more therapeutic polynucleotides are present on the same expression vector.

8. The method of claim 1, wherein the two or more therapeutic polynucleotides are present on two or more different expression vectors.

9. The method of claim 1, wherein expression of the two or more therapeutic polynucleotides is directed by a promoter suitable for activity in an avascular, aneural or low oxygen environment.

10. The method of claim 1, wherein the two or more therapeutic polynucleotides further comprise a therapeutic polynucleotide that is selected from the group consisting of Gata4, Mef2C, Tbx5, FGFR2, VEGF, MMP12, MMP14, forkhead, CD10, and a combination thereof.

* * * * *